US008291680B2

(12) United States Patent
Silvestri

(10) Patent No.: US 8,291,680 B2
(45) Date of Patent: Oct. 23, 2012

(54) APPARATUS AND METHOD FOR PROCESSING CONTAINER CLOSURES

(75) Inventor: Angelo Silvestri, Parma (IT)

(73) Assignee: Sidel S.p.A., Parma (IT)

( * ) Notice: Subject to any disclaimer, the term of this patent is extended or adjusted under 35 U.S.C. 154(b) by 0 days.

(21) Appl. No.: 12/601,775

(22) PCT Filed: Dec. 23, 2008

(86) PCT No.: PCT/IB2008/055511

§ 371 (c)(1), (2), (4) Date: Nov. 24, 2009

(87) PCT Pub. No.: WO2010/073064

PCT Pub. Date: Jul. 1, 2010

(65) Prior Publication Data

US 2011/0239590 A1 Oct. 6, 2011

(51) Int. Cl.

*B67B 1/03* (2006.01)
*B65B 57/10* (2006.01)
*A61L 2/00* (2006.01)

(52) U.S. Cl. ................ 53/426; 53/500; 53/290; 422/28; 422/302

(58) Field of Classification Search .................... 53/500, 53/498, 426, 490, 317, 167, 127, 287, 290, 53/306; 422/27, 28, 29, 301, 302, 304; 15/302, 15/304, 309.2

See application file for complete search history.

(56) References Cited

U.S. PATENT DOCUMENTS 1,857,075 A 5/1932 Wright et al.
2,501,291 A * 3/1950 Rue ................................ 53/141
3,455,644 A * 7/1969 Arber ............................ 422/302
3,833,339 A 9/1974 Pacilio
4,167,797 A * 9/1979 Wilde et al. ..................... 15/302
4,304,611 A * 12/1981 Ellis ................................ 134/23
5,321,934 A * 6/1994 Bech ............................... 53/478

(Continued)

FOREIGN PATENT DOCUMENTS

DE 30 09 202 A1 9/1981
DE 10 2005 032 332 A1 1/2007
JP 2007-338698 * 12/2008

*Primary Examiner* — Paul R Durand

(74) *Attorney, Agent, or Firm* — Pearne & Gordon LLP

(57) ABSTRACT

An apparatus (1) for processing container closures (2) comprises a sterilization unit (3), having a sterilization module (7) with means for spraying on the closures (2) a hot sterilization fluid, a capping unit (4), having screwing means active on the closures (2) for connecting them on correspondent containers, applying a predetermined torque, a guide member (5) configured in such a way to allow a plurality of closures (2) to be arranged therein and connected to the sterilization unit (3) and to the capping unit (4) to guide the closures (2) from the sterilization unit (3) to the capping unit (4), and means (13) for regulating the temperature of the closures (2) arranged in the guide member (5), to provide that the closures (2) have a predetermined desired temperature in the capping unit (4).

A method for processing container closures (2) comprises the following steps: sterilizing the closures (2) by spraying on the closures (2) a hot sterilization fluid, transferring the closures (2) from a sterilization unit (3) to a capping unit (4), by means of a guide member (5) interposed therein, screwing the closures (2) for connecting them on correspondent containers, applying a predetermined torque to the closures (2) in the capping unit (4), and regulating the temperature of the closures (2) arranged in the guide member (5), to provide that the closures (2) have a predetermined desired temperature in the capping unit (4).

20 Claims, 2 Drawing Sheets

U.S. PATENT DOCUMENTS 5,683,241 A * 11/1997 Casselman .................... 432/97
2005/0169796 A1* 8/2005 Krakers et al. ................ 422/28
2008/0200677 A1 8/2008 Stoessel et al.
2010/0275955 A1* 11/2010 Ueda et al. .................. 134/25.4

* cited by examiner

APPARATUS AND METHOD FOR PROCESSING CONTAINER CLOSURES

TECHNICAL FIELD AND BACKGROUND ART

The present invention relates to an apparatus and a method for processing container closures.

As generally known, in the food industry and in particular in the field of aseptic filling of containers with beverages and in the field of aseptic food packaging, there exists a need to sterilise the containers both internally and externally before they are filled.

Sterilisation is generally achieved using chemical agents, e.g. hydrogen peroxide, which can be used on surfaces of every type, such as paper, plastic, metal or organic materials.

To ensure that filling takes place in aseptic conditions it is necessary to sterilise not only the containers but also their closures, for example caps or stoppers, which serve to seal the containers at the end of the filling process.

In particular, the present invention is concerned with closures which are screwed to respective containers to be connected thereto.

Therefore, known apparatuses comprise a sterilization unit, for sterilizing the closures, and a capping unit, having screwing means active on the closures for connecting them on correspondent containers, applying a predetermined torque. Further, the sterilization unit comprises means for spraying on the closures a hot sterilization fluid. Depending on the sterilizing process that is implemented, the fluid can be heated so that it becomes vaporized. Therefore, the closures are heated during the sterilization step.

In addition, said apparatuses comprise a guide member, interposed between the sterilization unit and the capping unit.

The guide member is configured is such a way that a plurality of closures can be arranged in the guide member at the same time. This is important because the processing of the closures from the sterilization unit to the capping unit is run continuously, but the sterilization unit and the capping unit may have different processing rates. Hence, the guide member also acts as a buffer.

However, these known apparatuses have the following drawbacks.

Although the force applied to the closures in the capping unit, to screw them to the containers (closure torque), is the same for all the closures, the force required to open the containers, i.e. to remove the closures from the containers (opening torque) may vary greatly from case to case.

In fact, the opening torque of a given closure depends on the closure torque applied to that closure and on the temperature of the closure at the time the closure torque was applied (i.e. the temperature of the closures in the capping unit).

Hence, the temperature of the closures in the capping unit varies, depending on the time that undergoes since they exit from the sterilizing unit, i.e. the time the closures stay in the guide member.

In fact, as soon as the closures exit the sterilizing step, they begin to cool down, because they are not anymore subjected to the hot fluids present in the sterilization unit (i.e. the sterilization fluid and, in the case of dry sterilization technology, hot air having the purpose of drying the closures).

The dispersion of distribution of the temperature of the closures in the capping unit (from which the dispersion of distribution of the opening torque results) is particularly evident in case the apparatus is stopped as a consequence of a failure (or of any other reason).

In fact, in the case of a stop of the apparatus, the closures present in the sterilization unit are discharged (because they would be damaged if subjected to the hot sterilization fluids for too long) and the closures arranged in the guide member remain there until the cause of the stop is removed.

Therefore, one of the main drawbacks of the known apparatuses is that the opening torque is not uniform, with the consequence that some closures are too loose, and some others are too tight.

DISCLOSURE OF THE INVENTION

An object of the present invention is to eliminate the aforesaid drawbacks and to make available an apparatus and a method for processing container closures, which allows to sterilize container closures with a hot sterilization fluid and then screw them on corresponding containers in such a way that all the closures can be removed from the respective containers applying the same or about the same force. “Hot” or “heated”, in the present specification, means at any temperature above the ambient one (including the vaporization temperature).

An additional object is to make available an apparatus and a method for processing container closures, which allows a particularly low impact on the environment, avoiding a waste of energy.

Said objects are fully achieved by the apparatus of the present invention, which is characterised by the content of the claims set out below.

BRIEF DESCRIPTION OF DRAWINGS

These and other features shall become more readily apparent from the following description of a preferred embodiment, illustrated purely by way of non limiting example in the accompanying drawing tables, in which.

BEST MODE FOR CARRYING OUT THE INVENTION

Figure 1:
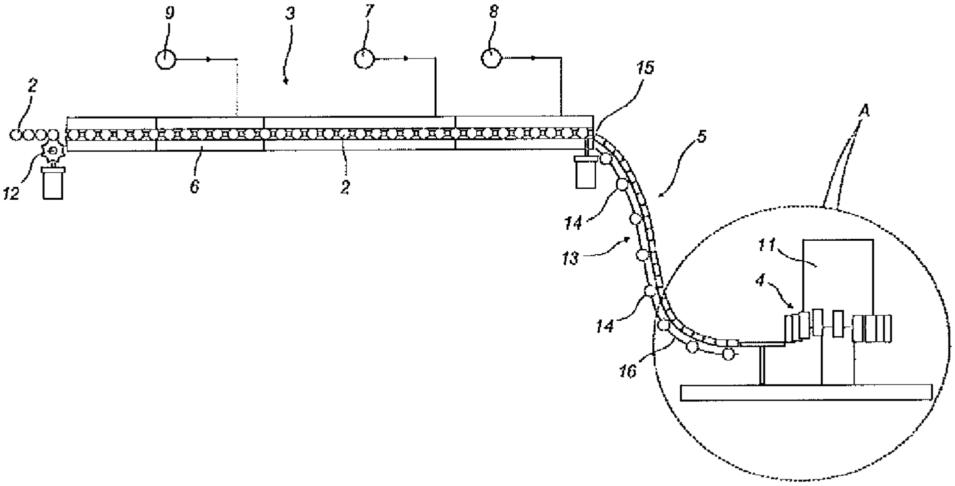
FIG. 1 shows schematically the apparatus according to the present application, in lateral view.

With reference to the Figures, the numeral 1 globally designates an apparatus for processing container closures 2, such as caps or stoppers, which serve to seal the containers and are applied to the containers after their filling.

The apparatus 1 comprises a sterilization unit 3, a capping unit 4 and a guide member 5 connected to the sterilization unit 3 and to the capping unit 4, in order to guide the closures from the sterilization unit 3 to the capping unit 4.

Hence, the apparatus 1 provides a sterilization of the closures 2 in the sterilization unit 3, a transfer of the closures 2 to the capping unit 4 and a connection of the closures 2 to corresponding containers in the capping unit 4.

The closures 2, after their exit from the sterilization unit 3 and before their entry in the capping unit 4, are arranged in the guide member 5.

In this light, the guide member 5 is configured in such a way to allow a plurality of closures to be arranged therein at the same time, thus providing a buffer interconnected between the sterilization unit 3 and the capping unit 4.

This is important because the processing of the closures 2 takes place in a continuous fashion, but the processing rate of the capping unit 4 may be different (typically higher) than that of the sterilization unit 3.

The sterilization unit 3 comprises a channel 6 through which the closures 2 are driven.

The sterilization unit 3 also has a sterilization module 7 with means for spraying on the closures 2 a hot sterilization fluid.

In particular, said spraying means of the sterilization module 7 are configured to inject said hot sterilization fluid inside the channel 6, according to a technology which is known in the art.

Hence, the sterilization unit 3 entails an increase in the temperature of the closures 2, which exit the sterilization unit 3 at a temperature $T_{out}$ which is higher that the temperature of the environment.

Preferably, the sterilization unit 3 comprises also drying means 8, active on the closures 2 downstream with respect to the sterilization means for drying the sterilization fluid condensed on the surface of the closures 2. In particular, the drying means comprises a drying module configured to inject hot sterilized air inside the channel 6, downstream with respect to the sterilization module 7.

Hence, the drying means preferably performs according to a drying technology, which is itself known in the art.

Preferably, but not necessarily the sterilization unit 3 also comprises a pre-heating module 9, configured to inject hot sterilized air inside the channel 6, upstream with respect to the sterilization module 7.

As regards the capping unit 4, it comprises screwing means 10 active on the closures 2 for connecting them on correspondent containers, applying a predetermined torque (closing torque).

Figure 2:
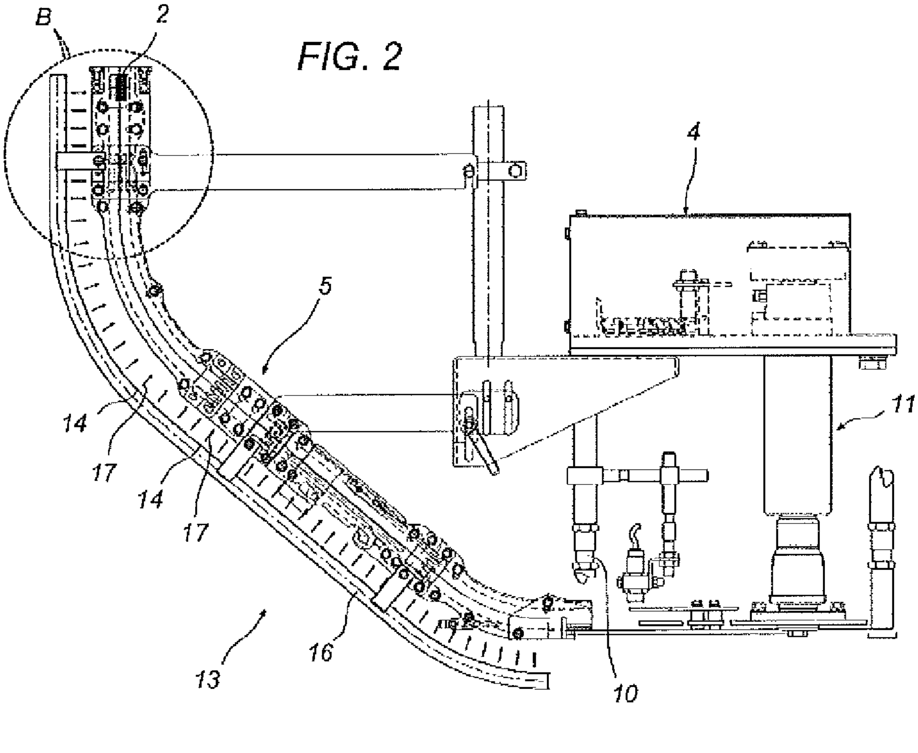
FIG. 2 shows an enlarged view of the portion indicated with A in FIG. 1.

The capping unit 4 preferably comprises a rotary capper 11 which is partially illustrated in FIGS. 1 and 2.

The capping unit 4 itself is designed according to a technology which is known in the art and will not be described in further detail.

However, it is noteworthy to observe that the capping unit 4 is preferably arranged at a lower level, with respect to the sterilization unit 3.

Therefore, the guide member 5 is preferably inclined downward from the sterilization unit 3 to the capping unit 4, to allow the closures 2 arranged in the guide member 5 to be subjected to the gravity force, pushing them towards the capping unit 4.

More preferably, the guide member 5 is configured to define a predetermined path for the closures 2; in particular, the guide member is shaped in such a way that it comprises:

a first portion, in correspondence with an outlet of the sterilization unit 3, which is arranged horizontally;

a second portion, in correspondence with an inlet of the capping unit 4, which is arranged horizontally and is at a lower level;

a third portion, which connects the first and the second ones, which is inclined or vertical.

Hence, the guide member 5 as a whole defines a path which is inclined downwards towards the capping unit 4.

Further, the apparatus 1 comprises an actuator 12 connected to a motorization and operatively active on the closures 2 to push them towards the sterilizing unit 3 and, hence, to the capping unit 4.

Preferably, the actuator 12 is arranged upstream the sterilizing unit 3 and applies its pushing force to all the closures arranged downstream (i.e. in the sterilizing unit 3 and in the guide member 5), which are aligned to form a continuous sequence, being substantially one in contact with the others set aside.

According to the invention, the apparatus 1 comprises means 13 (otherwise named "regulating means"), for regulating the temperature of the closures 2 arranged in the guide member 5, to provide that the closures 2 have a predetermined desired temperature in the capping unit 4.

Hence, said regulating means achieve the goal of stabilizing the temperature of the closures 2, then the closures 2 themselves are screwed to the respective containers.

In particular, the regulating means 13 comprises a plurality of nozzles 14 arranged in proximity of the guide member 5, to spray a sterilized fluid (regulation fluid) on the closures 2 contained therein. The regulation fluid sprayed on the closures 2 by the regulating means 13 is aimed at increasing or decreasing the temperature of the closures 2 arranged in the guide member 5. Preferably, the nozzles 14 are arranged along a path which follows the path defined by the guide member 5. In this way, de distance between the nozzles 14 and the closures 2 is minimized, thus optimizing the energy used by the regulating means 13, i.e. maximizing the performance of said means 13.

Preferably, the nozzles 14 are equally spaced along the path defined by the guide member. This advantageously allows the closures 2 arranged in the guide member 5 to receive the same amount of regulation fluid, in order to stabilize the temperature of the closures 2 in the capping unit 4.

The apparatus 1 also comprises means for holding for a predetermined amount of time the closures 2 arranged in the guide member 5 and for discharging the closures 2 contained in the sterilization unit 3.

These means, not illustrated in the drawings, are known in the art.

In practice, in case of a failure or any other event that entails the stop of the process (either the sterilization or the capping process), the flow of the containers is stopped.

Then, at an outlet station 15 of the sterilization unit 3, a gate is opened and the closures 2 contained in the sterilization unit 3 are discharged from the sterilization unit 3.

Since the flow of closures 2 in the apparatus 1 is stopped and until it is started again, the closures 2 arranged in the guide member 5 are hold therein. Hence, these closures 2 remain in the guide member 5 for a time (holding time) that is approximately equal to the time the apparatus 1 remains inactive.

In this light, the present invention provides a first a second embodiment, as regards the regulating means.

According to the first embodiment of the invention, the means 13 for regulating the temperature of the closures 2 arranged in the guide member 5 comprises heating means.

In particular, said heating means comprises nozzles 14 configured to blow heated and sterilized air on the closures arranged in the guide member 5.

Said heated and sterilized air is preferably conveyed under pressure into a conduit 16 provided with a plurality of apertures defining said nozzles 14. Therefore, in the first embodiment of the invention, the nozzles 14 are preferably defined by corresponding holes.

Figure 3:
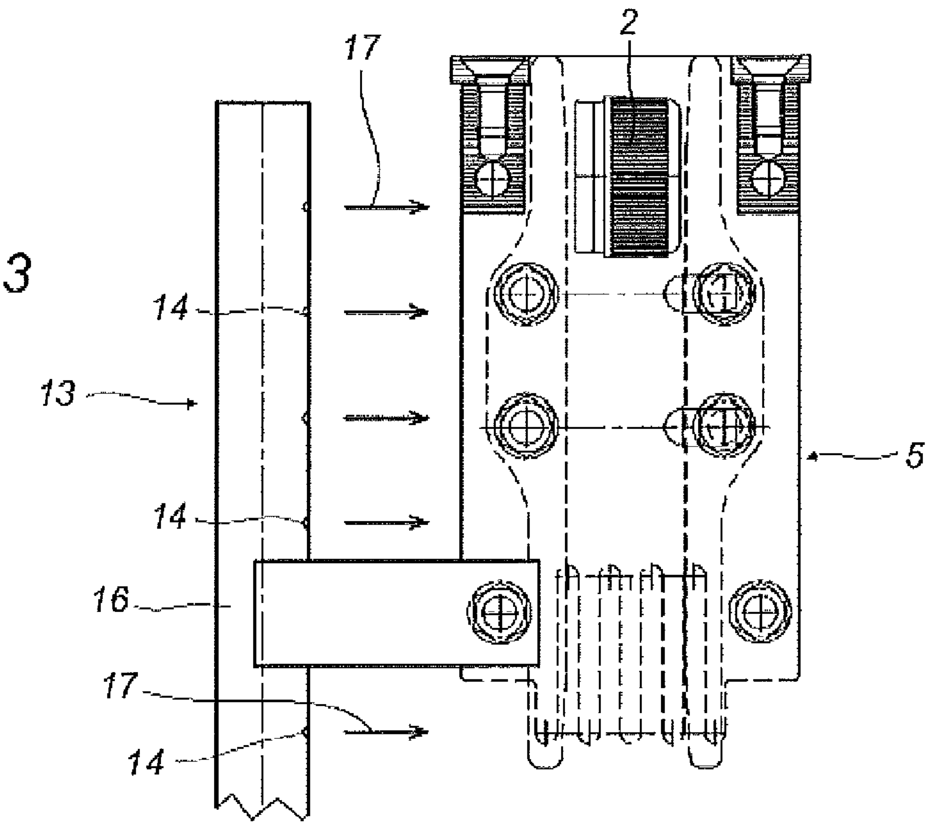
FIG. 3 shows an enlarged view of the portion indicated with B in FIG. 2.

In FIGS. 2 and 3, the arrows 17 indicate the orientation of the regulation fluid sprayed by the nozzles 14.

Preferably, said air (i.e. the regulation fluid) is heated at the temperature $T_{out}$ at which the closures 2 exit the sterilization unit 3. Therefore, said heating means preferably is configured to heat the closures 2 coupled to the guide member 5 at the temperature $T_{out}$ at which the closures 2 exit the sterilization unit 3.

It is noteworthy to observe that the heating means comprises a conduit to feed the nozzles 14 with hot fluid. Preferably, the heating means comprises a three way valve (not illustrated in the figure) inserted in the conduit, in order to allow the fluid flowing in the conduit to be directed away from the closures 2, if the heating fluid is not at the desired temperature.

Operatively, a temperature sensor inserted in the conduit detects the temperature of the fluid in the conduit. Until the detected temperature is lower than a predetermined desired value, the heating fluid is directed away from the closures 2 (operating the three way valve accordingly). When the detected temperature reaches the predetermined desired value, the heating fluid is directed towards the closures 2 through the nozzles 14 (operating the three way valve accordingly).

This advantageously accounts for the time delay of the heating means, i.e. for the time needed for the heating fluid of the heating means to reach the desired temperature value.

According to a further aspect of the present invention (first embodiment), the apparatus 1 comprises:

- a sensor (not illustrated in the figure) (e.g. a photo cell) for detecting a transit of the closures 2 in the guide member 5;
- control means connected to the means 13 and to the sensor, to trigger the activation of the heating means when the transit of closures 2 in the guide member 5 is interrupted.

The sensor is preferably arranged in the guide member 5.

Preferably, the control means are configured to:

- activate the regulating means 13 when the apparatus is stopped and the sensor detect an interruption of the transit of closures 2 in the guide member 5, in order to heat the closures 2 which remain in the guide member 5 for the holding time (and thus cooled down below the desired temperature); and
- stop the regulating means 13 when the sensor detect the transit of closures 2 in the guide member 5.

Alternatively, the apparatus 1 could comprise:

- a counter (not illustrated in the figures) for counting the closures 2 transferred to the capping unit 4 (from the guide member 5); and
- control means (not illustrated in the figures) connected to the means 13 and to the counter, to stop the heating means when the number of closures 2 transferred to the capping unit 4 while the heating means are active is equal (or higher) than the number of closures 2 arranged in the guide member at the time the apparatus was stopped.

Hence, the regulating means 13 are activated only when needed and stopped otherwise, in order not to waste energy.

As said before, the desired temperature is preferably set at a value which is approximately $T_{out}$ (the temperature value at which the closures 2 exit the sterilization unit 3), however such a desired value may be subjected to variations of about 10% with respect to $T_{out}$, without affecting the stability of the opening torque.

Preferably, the nozzles 14 are arranged at a single side of the guide member 5; more preferably, the nozzles 14 are configured to blow hot air towards the concave surfaces of the closures 2 arranged in the guide member 5, as this is illustrated on FIG. 3.

This allows advantageously to increase the efficiency of the regulating means 13.

According to a second embodiment of the invention, the means 13 for regulating the temperature of the closures 2 arranged in the guide member 5 comprises cooling means.

Preferably, the cooling means comprise two sets of nozzles 14 arranged at opposite sides of the guide member 5 to spray a cooling sterilized fluid on both sides of the closures 2. These nozzles 14 are configured to spray nebulised cooling liquid. In this configuration, the cooling fluid is preferably dispensed through conventional nozzles.

According to this second embodiment, said cooling fluid may be obtained in three different ways, each one implementing a first step to obtain a sterile fluid and a second step to cool the sterile fluid through a cooler exchange.

The first way entails the use of a filter to sterilize liquid water during the first step; the liquid water is then cooled down to a desired predetermined temperature during the second step.

The second way entails the use of a UHT device to produce a sterilized-cooling fluid; during the first step, the device has to sterilize the fluid (such as water), heating it at a given temperature for a defined time to guarantee the sterility; and then during the second step, the device has to cool the water down to a defined temperature value.

The third way entails the use of a condenser, to transform a hot vapour (sterilized because at high temperature) into water (i.e. a cooling sterilized fluid) during the first step, followed by a cooling to a defined temperature value during the second step.

In any case, it must be observed that the cooling means must be active during the operation of the apparatus 1.

In this light, the first embodiment of the invention has the advantage that less energy is required, because the heating means are activated only for relatively short time periods (in correspondence of the inactivity of the apparatus).

The present invention makes available also a method for processing container closures 2.

Said method comprises the following steps:

- sterilizing the closures 2 by spraying on the closures 2 a hot sterilization fluid;
- transferring the closures 2 from a sterilization unit 3 to a capping unit 4, by means of a guide member 5 interposed therein;
- screwing the closures 2 for connecting them on correspondent containers, applying a predetermined torque (closing torque) to the closures 2 in the capping unit 4.

According to the invention, the method further comprises a step of regulating the temperature of the closures 2 arranged in the guide member 5, to provide that the closures 2 have a predetermined desired temperature in the capping unit 4.

Therefore, the method entails a continuous flow of closures 2 from the sterilization unit 3 to the capping unit 4. The speed of the closures 2 in this flow may vary during the path followed by the closures 2 in the flow itself, because the guide member acts as a buffer element interposed between the sterilization unit 3 and the capping unit 4.

Additionally, the method comprises the following possible steps:

- holding for a predetermined time the closures 2 arranged in the guide member 5 (said predetermined time is the time interval during which the apparatus remains inactive, i.e. the flow of closures 2 from the sterilization unit 3 to the capping unit 4 is interrupted);
- discharging the closures 2 contained in the sterilization unit 3.

These steps are executed in case of a stop of the apparatus, caused by a failure or by any other event (e.g. a filling machines feeding containers to the capping unit 4 is stopped).

According to the first embodiment of the invention, the regulating step is a step of heating the closures 2 arranged in the guide member 5.

According to the first embodiment of the invention, the sterilization step to comprises preferably a step of drying the closures 2 after the spraying step and, possibly (but not necessarily), a step of pre-heating the closures 2 before the spraying step.

According to the first embodiment of the invention, the heating step entails preferably the blowing of hot sterilized air on the closures arranged in the guide member 5.

As regards the step of providing said hot air (constituting the regulation fluid in the first embodiment), reference is made to the description of the apparatus 1 reported above.

According to the first embodiment of the invention, the method additionally provides a step of sensing the transit of the closures 2 towards the capping unit 4, an activation of the heating step being triggered when the transit of the closures 2 is interrupted. Said interruption means that the apparatus is stopped for some reason; therefore, the closures arranged in the guide member 5 would cool down significantly with respect to the temperature at the outlet of the sterilizing unit.

For instance, the heating means is then activated for a predetermined time duration, to secure that the closures 2 arranged in the guide member 5 reach the desired predetermined temperature.

At that time, the transit of the closures may be started back again.

According to a further aspect of the present invention (pertinent to the first embodiment of the invention), the method additionally provides a step of counting the closures 2 transferred to the capping unit 4, and a step of stopping (i.e. disabling) the heating step when the number of closures 2 transferred to the capping unit 4 during the heating step is equal or higher than the number of closures 2 arranged in the guide member 5.

In fact, in this way it is provided that all the closures 2 which were hold in the guide member 5 during the period of inactivity of the apparatus (while the flow of closures was interrupted) have already been transferred to the capping unit 4; hence, the successive closures 2 have not been hold still in the guide member 5, and therefore it can be assumed that their temperature has approximately the value $T_{out}$ (i.e. the temperature value at which the closures 2 exit the sterilization unit 3).

In this light, the heating step preferably entails a heating of the closures 2 at the temperature value $T_{out}$, i.e. the temperature value at which the closures 2 exit the sterilization unit 3.

According to the second embodiment of the invention, the regulating step is a step of cooling the closures 2 arranged in the guide member 5.

Preferably, the cooling step entails a step of spraying a cooling fluid (preferably sterilized water) on the closures 2 arranged in the guide member 5, preferably by means of a double set of nozzles 14 arranged at opposite sides of the guide member 5.

The present invention provides the following advantages.

It allows to sterilize closures 2 and to screw them on corresponding containers, in such a way that the sealed containers have an increased quality, because they are provided with an opening torque of predetermined, desired value.

In particular, the present invention allows to make sure that the opening torque of the closures screwed to the corresponding containers is not too low (avoiding the risk of bad sealing of the container) not too tight (avoiding the risk that the container is difficult to open by hand).

Thus, the distribution of the opening torque of the closures screwed to the corresponding containers has a particularly low variance with respect to the desired average value.

These advantages are achieved by means of the presence of the means 13 for regulating the temperature of the closures 2 arranged in the guide member 5. In fact, this allows a stability of the temperature of the closures 2 in the capping unit 4, i.e. of the temperature of the closures 2 at the time they are screwed on the corresponding containers (in combination with the fact that the closing torque applied to the closures is constant).

Furthermore, said advantages can be achieved with a dry technology (i.e. dry sterilization of the closures), thanks to the fact that the closures 2 are heated to a predetermined value.

In this light, a further advantage of the present invention is that it allows the aforementioned results with a particularly low environmental impact, avoiding any waste of energy.

This advantage is achieved by means of said control means, which allow to activate the regulating means 13 only for limited time periods, in correspondence of periods of inactivity of the apparatus (i.e. of interruption of the flow of the closures 2).

This advantage is additionally achieved by the configuration of said means 13, which maximizes their efficiency.

LIST OF FIGURE ELEMENTS

1) Apparatus
2) Closures
3) Sterilization unit
4) Capping unit
5) Guide member
6) Channel of 3
7) Sterilization module of 3
8) Drying module of 3
9) Pre-heating module of 3
10) Screwing means of 4
11) Rotary capper of 4
12) Actuator
13) Regulating means
14) Nozzles of 13
15) Outlet station
16) Conduit of 13
17) Arrows (orientation of the regulation fluid sprayed by 14)

The invention claimed is:

1. Method for processing container closures (2), comprising the following steps:

sterilizing the closures (2) by spraying on the closures (2) a hot sterilization fluid;

transferring the closures (2) from a sterilization unit (3) to a capping unit (4), by means of a guide member (5) interposed therein;

screwing the closures (2) for connecting them on correspondent containers, applying a predetermined torque to the closures (2) in the capping unit (4), characterized in that it comprises:

a step of regulating the temperature of the closures (2) fed to the capping unit (4) arranged in the guide member (5), to provide that the closures (2) have a predetermined desired temperature in the capping unit (4), the regulating step being a step of heating the closures (2) arranged in the guide member (5);

a step of sensing the transit of the closures (2) towards the capping unit (4), an activation of the heating step being triggered when the transit of the closures (2) is interrupted.

2. Method according to claim 1, wherein the regulating step is a step of regulating the temperature of the closures (2) arranged in the guide member (5).

3. Method according to claim 1, comprising the following steps:

holding for a predetermined time the closures (2) associated to the guide member (5);

discharging the closures (2) contained in the sterilization unit (3).

4. Method according to claim 1, wherein the sterilization step comprises a step of drying the closures (2) after the spraying step and wherein the heating step entails the blowing of hot sterilized air on the closures (2) arranged in the guide member (5).

5. Method according to claim 1, comprising a step of counting the closures (2) transferred to the capping unit (4), the heating step being stopped when the number of closures (2) transferred to the capping unit (4) during the heating step is equal to or higher than the number of closures (2) arranged in the guide member (5).

6. Method according to claim 1, wherein the closures (2) are heated at the temperature ($T_{out}$) at which the closures (2) exit the sterilization unit (3).

7. Method for processing container closures (2), comprising the following steps:

sterilizing the closures (2) by spraying on the closures (2) a hot sterilization fluid;

transferring the closures (2) from a sterilization unit (3) to a capping unit (4), by means of a guide member (5) interposed therein;

screwing the closures (2) for connecting them on correspondent containers, applying a predetermined torque to the closures (2) in the capping unit (4), characterized in that it comprises:

a step of regulating the temperature of the closures (2) fed to the capping unit (4) arranged in the guide member (5), to provide that the closures (2) have a predetermined desired temperature in the capping unit (4); the regulating step being a step of heating the closures (2) arranged in the guide member (5);

a step of counting the closures (2) transferred to the capping unit (4), the heating step being stopped when the number of closures (2) transferred to the capping unit (4) during the heating step is equal to or higher than the number of closures (2) arranged in the guide member (5).

8. Apparatus (1) for processing container closures (2), comprising:

a sterilization unit (3) having a sterilization module (7) with means for spraying on the closures (2) a hot sterilization fluid;

a capping unit (4) having screwing means (10) active on the closures (2) for connecting them on correspondent containers, applying a predetermined torque;

a guide member (5) configured in such a way to allow a plurality of closures (2) to be arranged therein and connected to the sterilization unit (3) and to the capping unit (4) to guide the closures (2) from the sterilization unit (3) to the capping unit (4), characterized in that it comprises:

means (13) for regulating the temperature of the closures (2) fed to the capping unit (4), to provide that the closures (2) have a predetermined desired temperature in the capping unit (4); said means (13) for regulating the temperature of the closures arranged in the guide member comprising heating means;

a sensor for detecting a transit of the closures (2) in the guide member (5); and control means connected to the heating means and to the sensor, configured to trigger the activation of the heating means when the transit of closures (2) is interrupted.

9. Apparatus according to claim 8, wherein said means (13) for regulating the temperature of the closures (2) are operatively active on the closures (2) arranged in the guide member (5).

10. Apparatus according to claim 8, wherein the guide member (5) is inclined downward from the sterilization unit (3) to the capping unit (4).

11. Apparatus according to claim 8, wherein said means (13) for regulating the temperature comprises a plurality of nozzles (14) arranged in proximity of the guide member (5) to spray a sterilized fluid on the closures (2) arranged in the guide member (5).

12. Apparatus according to claim 11, wherein the nozzles (14) are equally spaced along the path defined by the guide member (5).

13. Apparatus according to claim 8, wherein the heating means is configured to heat the closures (2) coupled to the guide member (5), at the temperature ($T_{out}$) at which the closures (2) exit the sterilization unit (3).

14. Apparatus according to claim 8, comprising:

a counter for counting the closures (2) transferred to the capping unit (4);

control means connected to the heating means and to the counter, to stop the heating means when the number of closures (2) transferred to the capping unit (4) while the heating means is active is equal or higher than the number of closures (2) coupled to the guide member (5).

15. Apparatus according to claim 8, comprising drying means (8) active on the closures (2) downwards with respect to the sterilization module (7), said heating means comprising nozzles (14) configured to blow heated and sterilized air on the closures (2) arranged in the guide member (5).

16. Apparatus according to claim 15, wherein said nozzles (14) are configured to blow hot air towards the concave surfaces of the closures (2) arranged in the guide member (5).

17. Apparatus according to claim 8, comprising means for holding for a predetermined time the closures (2) associated to the guide member (5) and discharging the closures (2) contained in the sterilization unit (3).

18. Apparatus (1) for processing container closures (2), comprising:

a sterilization unit (3) having a sterilization module (7) with means for spraying on the closures (2) a hot sterilization fluid;

a capping unit (4) having screwing means (10) active on the closures (2) for connecting them on correspondent containers, applying a predetermined torque;

a guide member (5) configured in such a way to allow a plurality of closures (2) to be arranged therein and connected to the sterilization unit (3) and to the capping unit (4) to guide the closures (2) from the sterilization unit (3) to the capping unit (4), characterized in that it comprises:

means (13) for regulating the temperature of the closures (2) fed to the capping unit (4), to provide that the closures (2) have a predetermined desired temperature in the capping unit (4); said means (13) for regulating the temperature of the closures arranged in the guide member comprising heating means;

a counter for counting the closures (2) transferred to the capping unit (4);

control means connected to the heating means and to the counter, to stop the heating means when the number of closures (2) transferred to the capping unit (4) while the heating means is active is equal or higher than the number of closures (2) coupled to the guide member (5).

19. Apparatus (1) for processing container closures (2), comprising:

a sterilization unit (3) having a sterilization module (7) with means for spraying on the closures (2) a hot sterilization fluid;

a capping unit (4) having screwing means (10) active on the closures (2) for connecting them on correspondent containers, applying a predetermined torque;

a guide member (5) configured in such a way to allow a plurality of closures (2) to be arranged therein and connected to the sterilization unit (3) and to the capping unit (4) to guide the closures (2) from the sterilization unit (3) to the capping unit (4), characterized in that it comprises:

means (13) for regulating the temperature of the closures (2) fed to the capping unit (4), to provide that the closures (2) have a predetermined desired temperature in the capping unit (4); said means (13) for regulating the temperature of the closures arranged in the guide member comprising heating means;

drying means (8) active on the closures (2) downwards with respect to the sterilization module (7), said heating means comprising nozzles (14) configured to blow heated and sterilized air on the closures (2) arranged in the guide member (5), said nozzles (14) being configured to blow hot air towards the concave surfaces of the closures (2) arranged in the guide member (5).

20. Apparatus (1) for processing container closures (2), comprising:

a sterilization unit (3) having a sterilization module (7) with means for spraying on the closures (2) a hot sterilization fluid;

a capping unit (4) having screwing means (10) active on the closures (2) for connecting them on correspondent containers, applying a predetermined torque;

a guide member (5) configured in such a way to allow a plurality of closures (2) to be arranged therein and connected to the sterilization unit (3) and to the capping unit (4) to guide the closures (2) from the sterilization unit (3) to the capping unit (4), characterized in that it comprises:

means (13) for regulating the temperature of the closures (2) fed to the capping unit (4), to provide that the closures (2) have a predetermined desired temperature in the capping unit (4); said means (13) for regulating the temperature of the closures (2) arranged in the guide member comprises cooling means, the cooling means comprise two sets of nozzles (14) arranged at opposite sides of the guide member (5) to spray a cooling sterilized fluid on the closures (2).

* * * * *